(12) United States Patent
Kontaxis et al.

(10) Patent No.: US 11,260,245 B2
(45) Date of Patent: Mar. 1, 2022

(54) SYSTEM AND METHOD FOR DETERMINING ARC DOSE FOR ARC THERAPY

(71) Applicant: Electa AB (Publ), Stockholm (SE)

(72) Inventors: Charis Kontaxis, Utrecht (NL);
Gijsbert Herman Bol, Utrecht (NL);
Bas Willem Raaymakers, Utrecht (NL)

(73) Assignee: ELEKTA AB (PUBL), Stockholm (SE)

( * ) Notice: Subject to any disclaimer, the term of this patent is extended or adjusted under 35 U.S.C. 154(b) by 0 days.

(21) Appl. No.: 16/973,124

(22) PCT Filed: Jun. 3, 2019

(86) PCT No.: PCT/IB2019/054585
§ 371 (c)(1),
(2) Date: Dec. 8, 2020

(87) PCT Pub. No.: WO2020/003026
PCT Pub. Date: Jan. 2, 2020

(65) Prior Publication Data
US 2021/0252307 A1     Aug. 19, 2021

Related U.S. Application Data

(60) Provisional application No. 62/692,235, filed on Jun. 29, 2018.

(51) Int. Cl.
*A61N 5/10*     (2006.01)
(52) U.S. Cl.
CPC ......... *A61N 5/1031* (2013.01); *A61N 5/1038* (2013.01); *A61N 5/1047* (2013.01);
(Continued)

(58) Field of Classification Search
None
See application file for complete search history.

(56) References Cited

U.S. PATENT DOCUMENTS

2009/0225942 A1\*   9/2009   Shepard ............... A61N 5/1047
378/65
2013/0193351 A1\*   8/2013   Cheng ................. A61N 5/1047
250/492.1

(Continued)

FOREIGN PATENT DOCUMENTS

EP     3126001 B1     2/2017

OTHER PUBLICATIONS

International Search Report and Written Opinion dated Sep. 18, 2019 in International Application No. PCT/IB2019/054585, 18 pages.

*Primary Examiner* — Hoon K Song
(74) *Attorney, Agent, or Firm* — Finnegan, Henderson, Farabow, Garrett & Dunner, LLP (57) ABSTRACT

Systems and methods are provided for radiation delivery. An exemplary method includes receiving an image depicting anatomical data of a target region of patient tissue and determining an initial prescribed dose of radiotherapeutic radiation to be delivered to the target region. The method also includes discretizing the arc for VMAT into a plurality of arc segments and performing an iteration process for determining an arc dose according to radiation delivered in the arc segments. The method further includes determining whether a condition for terminating the iteration process is met and terminating the iteration process based on a result of the determination that the condition for terminating the iteration process is met.

20 Claims, 6 Drawing Sheets

(52) U.S. Cl.
CPC .... *A61N 5/1067* (2013.01); *A61N 2005/1054* (2013.01); *A61N 2005/1055* (2013.01); *A61N 2005/1058* (2013.01); *A61N 2005/1061* (2013.01)

(56) References Cited

U.S. PATENT DOCUMENTS

| | | | |
|---|---|---|---|
| 2013/0301893 A1* | 11/2013 | Netsch | G06T 7/12 |
| | | | 382/131 |
| 2016/0339268 A1 | 11/2016 | Bzdusek et al. | |
| 2017/0354393 A1 | 12/2017 | Bose et al. | |
| 2018/0099151 A1* | 4/2018 | Sullivan | A61N 5/1039 |
| 2020/0353286 A1* | 11/2020 | Wu | A61N 5/1038 |

\* cited by examiner

SYSTEM AND METHOD FOR DETERMINING ARC DOSE FOR ARC THERAPY

CROSS REFERENCE TO RELATED APPLICATIONS

This application is a national stage application of International Application No. PCT/IB2019/054585, filed Jun. 3, 2019, which claims the benefit of priority to U.S. Provisional Application No. 62/692,235 filed Jun. 29, 2018, the contents of which are expressly incorporated herein by reference to their entireties.

TECHNICAL FIELD

The disclosure generally relates to radiation therapy or radiotherapy. More specifically, this disclosure relates to systems and methods for determining arc dose for an arc therapy during radiation therapy.

BACKGROUND

Volumetric modulated arc therapy (VMAT) is a radiation therapy treatment technique aiming to deliver highly conformal radiation treatment. In a VMAT treatment, as a gantry rotates around the patient, a radiation source attached to the gantry emits beams having changing shapes and intensities. Creating individual patient VMAT treatment plans is generally a trial-and-error process. The radiation dose delivered to a target region may be weighed against the effect of radiation on patient organs. Furthermore, treatment plans are adjusted by manipulating program constraints and then recalculating an exposure map. The effects of these manipulations on the recalculated exposure map may be difficult to anticipate. For example, even the order in which program constraints are adjusted may affect the exposure map. As a result, treatment plans can depend on the subjective judgments of experienced practitioners. Even the most skilled practitioners cannot guarantee the optimality of treatment plans, or whether additional effort may identify a better plan.

Therefore it may be desirable to develop improved treatment planning systems and methods that track and adjust the dose delivered to the target region in arc treatments in real time.

SUMMARY

In one aspect, the present disclosure involves radiotherapeutic apparatus for volumetric modulated arc therapy (VMAT). The radiotherapeutic apparatus includes a gantry configured to rotate along a trajectory, the trajectory comprising an arc for VMAT, the arc comprising a plurality of control points, and an imaging device configured to capture one or more images depicting anatomical data of a patient. The radiotherapeutic apparatus may also include a controller configured to perform operations comprising: receiving an image depicting anatomical data of a target region of patient tissue; determining an initial prescribed dose of radiotherapeutic radiation to be delivered to the target region; discretizing the arc for VMAT into a plurality of arc segments, each of the arc segments being between two consecutive control points of the plurality of control points; performing an iteration process including at least one iteration. Each iteration of the iteration process includes: for each of the plurality of arc segments: performing a fluence optimization process using the anatomical data of the target region and the target region data to generate a distribution profile for a sub-dose to be delivered for the each of the plurality of arc segments based on one of the initial prescribed dose, an updated prescribed dose, and/or a bias dose that is determined based on the anatomical data of the target region; segmenting the sub-dose distribution profile into segments for delivery the sub-dose to the target region; identifying, among the segments, one or more non-deliverable segments, each of the one or more non-deliverable segments violating a constraint of the radiotherapeutic apparatus; replacing the each of the one or more non-deliverable segments with an updated segment, where the updated segment does not violate a mechanical or efficiency constraint of the radiotherapeutic apparatus; determining an arc dose based on the updated segments and the selected segments that do not violate a mechanical and/or efficiency constraint of the radiotherapeutic apparatus; delivering radiation to the target region with the determined arc dose along the arc; subtracting the determined arc dose from the prescribed dose to generate an updated prescribed dose. The operations performed by the controller may further include determining whether a condition for terminating the iteration process is met and terminating the iteration process based on a result of the determination that the condition for terminating the iteration process is met.

In another aspect, the present disclosure involves a method for radiation delivery to a target region of a patient using a VMAT device. The method comprises: receiving an image depicting anatomical data of a target region of patient tissue; determining an initial prescribed dose of radiotherapeutic radiation to be delivered to the target region; discretizing the arc for VMAT into a plurality of arc segments, each of the arc segments being between two consecutive control points of the plurality of control points; performing an iteration process including at least one iteration. Each iteration of the iteration process includes: for each of the plurality of arc segments: performing a fluence optimization process using the anatomical data of the target region and the target region data to generate a distribution profile for a sub-dose to be delivered for the each of the plurality of arc segments based on one of the initial prescribed dose, an updated prescribed dose, and/or a bias dose that is determined based on the anatomical data of the target region; segmenting the sub-dose distribution profile into segments for delivery the sub-dose to the target region; identifying, among the segments, one or more non-deliverable segments, each of the one or more non-deliverable segments violating a constraint of the radiotherapeutic apparatus; replacing the each of the one or more non-deliverable segments with an updated segment, where the updated segment does not violate a mechanical or efficiency constraint of the radiotherapeutic apparatus; determining an arc dose based on the updated segments and the segments that do not violate a mechanical and/or efficiency constraint of the radiotherapeutic apparatus; delivering radiation to the target region with the determined arc dose along the arc; subtracting the determined arc dose from the prescribed dose to generate an updated prescribed dose. The method further comprises determining whether a condition for terminating the iteration process is met and terminating the iteration process based on a result of the determination that the condition for terminating the iteration process is met.

In a further aspect, the present disclosure involves a non-transitory computer-readable medium that stores a set of instructions that is executable by at least one processor of a device to cause the device to perform a method comprising: receiving an image depicting anatomical data of a target region of patient tissue; determining an initial prescribed dose of radiotherapeutic radiation to be delivered to the target region; discretizing the arc for VMAT into a plurality of arc segments, each of the arc segments being between two consecutive control points of the plurality of control points; performing an iteration process including at least one iteration. Each iteration of the iteration process includes: for each of the plurality of arc segments: performing a fluence optimization process using the anatomical data of the target region and the target region data to generate a distribution profile for a sub-dose to be delivered for the each of the plurality of arc segments based on one of the initial prescribed dose, an updated prescribed dose, and/or a bias dose that is determined based on the anatomical data of the target region; segmenting the sub-dose distribution profile into segments for delivery the sub-dose to the target region; identifying, among the segments, one or more non-deliverable segments, each of the one or more non-deliverable segments violating a constraint of the radiotherapeutic apparatus; replacing the each of the one or more non-deliverable segments with an updated segment, where the updated segment does not violate a mechanical or efficiency constraint of the radiotherapeutic apparatus; determining an arc dose based on the updated segments and the selected segments that do not violate a mechanical and/or efficiency constraint of the radiotherapeutic apparatus; delivering radiation to the target region with the determined arc dose along the arc; subtracting the determined arc dose from the prescribed dose to generate an updated prescribed dose. The method further comprises determining whether a condition for terminating the iteration process is met and terminating the iteration process based on a result of the determination that the condition for terminating the iteration process is met.

Additional objects and advantages of the present disclosure will be set forth in part in the following detailed description, and in part will be obvious from the description, or may be learned by practice of the present disclosure. The objects and advantages of the present disclosure will be realized and attained by means of the elements and combinations particularly pointed out in the appended claims.

It is to be understood that the foregoing general description and the following detailed description are exemplary and explanatory only, and are not restrictive of the disclosure, as claimed.

BRIEF DESCRIPTION OF THE DRAWINGS

In the drawings, which are not necessarily drawn to scale, like numerals may describe similar components in different views. Like numerals having letter suffixes or different letter suffixes may represent different instances of similar components. The drawings generally illustrate, by way of example, but not by way of limitation, various embodiments, and together with the description and claims, serve to explain the disclosed embodiments. When appropriate, the same reference numbers are used throughout the drawings to refer to the same or like parts. Such embodiments are demonstrative and not intended to be exhaustive or exclusive embodiments of the present apparatuses, systems, or methods.

DETAILED DESCRIPTION

Figure 1:
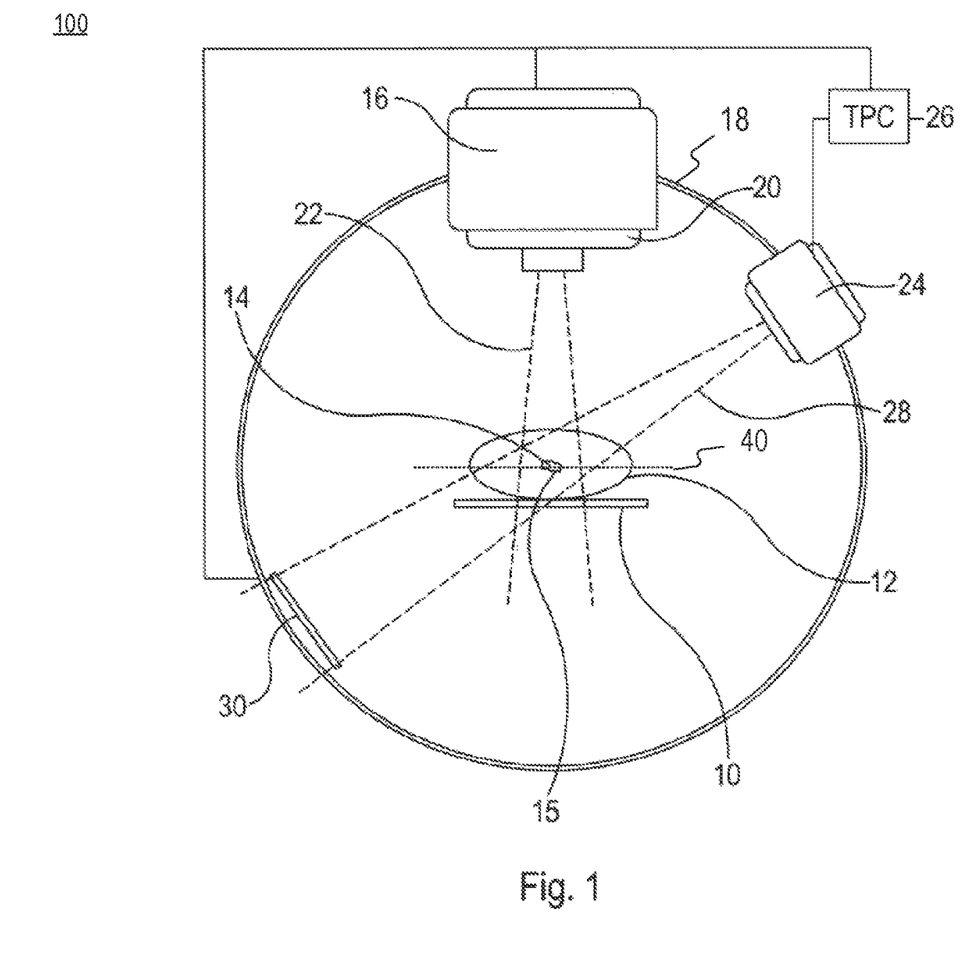
FIG. 1 is a block diagram of an exemplary radiotherapy system, consistent with disclosed embodiments.

FIG. 1 shows an exemplary radiotherapy system, consistent with disclosed embodiments. Radiotherapy system 100 includes a patient table 10, a therapy radiation source 16, therapy radiation beam 22, a collimator set 20, a treatment planning computer (TPC) 26, an imaging radiation source 24, and an image acquisition device 30.

Patient table 10 is configured to support a patient 12. Patient table 10 may be moveable (within limits) in any of its six degrees of freedom, e.g., three translational directions and three rotational directions, so as to place the desired part of the patient that is to be treated at a specific location 14 within the treatment room, relative to the machine, known as the "isocenter." This may be made visible by a number of low-power lasers mounted at fixed locations and directed towards isocenter 14. Isocenter 14 corresponds to the intersection of rotational axis of rotatable gantry 18 and beam axis. The patient table may be so positioned that the isocenter 14 lies within the outline of a target region 15, such as a tumor. In some embodiments, target region 15 may include a tumor region and an organs-at-risk (OAR) region.

Therapy radiation source 16 is configured to be mounted on a gantry (not visible) extending from a rotatable gantry 18. Therapy radiation source 16 may be configured to emit high-energy x-rays, or an electron beam, or a selectable choice of both, or another form of radiation. In some embodiments, therapy radiation source 16 may be a linear accelerator (linac).

Rotatable gantry 18 may be configured to be set into a wall or other structure so that the operating machinery can be concealed. Therapy radiation source 16 may extend from a support at a point offset from a horizontal axis 40 and may be directed towards horizontal axis 40 and the isocenter 14. Thus, as rotatable gantry 18 rotates, therapy radiation source 16 illuminates the region around the isocenter 14 from all possible radial directions. In some embodiments, therapy radiation source 16 may emit therapy radiation beam 22 continuously when rotatable gantry 18 rotates. Rotatable gantry 18 may rotate around horizontal axis 40 that passes through the isocenter 14 along a trajectory. For example, rotatable gantry 18 may rotate along an arc, which may be a single 360 degrees or a portion thereof (e.g., 180 degrees or 120 degrees). This provides one way in which the apparatus limits the radiation dose applied to healthy tissue while maintaining the dose applied to the tumor or other lesion being treated; the lesion (or relevant part of it) can be exposed during the entirety of the treatment, but the surrounding tissue will only be exposed when directly in line with the beam.

In some embodiments, for a VMAT treatment, a gantry rotation (i.e., rotatable gantry 18 rotates along an arc) includes a plurality of discrete beam angles. For instance, a gantry rotation may include a 360-degree circle or arc, which may be divided into increments for determining discrete beam angles, such as two increments of 180 that each yield 180 discrete beam angles. The beam angles may be uniformly spaced (e.g., 2 degrees apart). Alternatively, the beam angles may be spaced unevenly. For each beam angle, a set of parameters may be determined according to a treatment plan. For example, a set of multi-leaf collimator (MLC) leaf positions, MLC shape, gantry rotation speed, gantry position, dose rate, and/or any other parameters at a specific beam angle may be specified in the treatment plan. In some embodiments, each beam angle may correspond to a control point. A control point may define the parameters that control the therapy at a particular beam angle. For example, the control point may include a parameter reflecting a position of rotatable gantry 18, the dose that is to be delivered between this and the next (or previous) control point, and the shape of the MLC at that control point. Each control point may define one beam, which may be decomposed into a matrix of beamlets. For example, a beamlet may be 3×10 mm$^2$ or 3×5 mm$^2$. The radiation therapy treatment plan may then be evaluated by considering the dose distribution over a discretization of the irradiated area into a number of cubes (e.g., voxels). Thus, TPC 26 may perform a process for updating an existing radiation therapy treatment plan using a dose distribution as a treatment objective. The existing radiation therapy treatment plan may include a known dose distribution. Additionally, the existing radiation therapy treatment plan may include an initial set of control points. In some embodiments, TPC 26 may optimize the control points to approximate the known dose distribution.

Collimator set 20 is configured to regulate the cross-sectional intensity and/or shape of the radiation beams emitted from therapy radiation source 16. Collimator set 20 may be integrated with therapy radiation source 16 and act on therapy radiation beam 22 produced by therapy radiation source 16 to limit lateral extent. Collimator set 20 may include two pairs of collimators, each acting in mutually transverse directions to limit therapy radiation beam 22 in multiple directions. The first pair of collimators may be a block collimator, comprising a pair of collimating sections which are moveable back and forth in an x-direction and have a flat front face substantially parallel with the y-direction. By moving the blocks back and forth, therapy radiation beam 22 can be limited in the x-direction as desired. The second pair of collimators may be MLCs. The MLC may include two opposed banks of leaves. Each leaf may be extendable back and forth in the y-direction and being relatively long in the y-direction, allowing the leaf to reach across a significant proportion of the beam width, relatively deep in the z-direction so as to allow it to attenuate the beam significantly, and relatively narrow in the x-direction so as to allow a good resolution. By moving individual leaves to the desired position, each bank of leaves as a whole can present a front edge that takes up substantially any shape.

Between the two pairs of collimators, therapy radiation beam 22 can be delimited to substantially any required shape, with the block collimator defining the lateral extent of the shape in the x-direction and the MLC defining the remaining part of the shape. In combination with the rotational movement of therapy radiation source 16, collimator set 20 may allow a complex three-dimensional dose distribution to be built up within the patient, in line with the prescription developed by the patient's clinician. In standard practice, oncologists prescribe a radiation dose that allows a certain percentage of volume in healthy tissue to be sacrificed in order to make sufficient progress in treating the adjacent target region, such as a cancerous tumor. A typical dose might be, for example, that the target region is to receive a radiation dose of 80 Gy (where "Gy" is the shorthand for "Gray" the international unit for radiation dose absorption), whilst no more than 30% volume of an adjacent organ can exceed a radiation dose of 20 Gy. The prescribed dose distribution results from multiple beams of different shapes and different directions of arrival which are produced by varying the angle at which the source irradiates the patient, the dose rate of radiation emitted from therapy radiation source 16, and the shape outlined by collimator set 20 during treatment, either stepwise or continuously.

TPC 26 is configured to determine and generate creating a treatment plan for delivering a dose distribution via radiotherapy system 100 according to a prescribed dose to be delivered. For example, TPC 26 may be configured to determine various parameters for the components of radiotherapy system 100, such as a set of MLC leaf positions, MLC shape, gantry rotation speed, gantry position, dose rate, and/or any other parameters. A prescribed dose may be in the form of a dose distribution. The dose distribution may be a three-dimensional map showing the areas which receive a specified dose of radiation (e.g., a lesion), the areas in which the dose should be minimized to the extent possible, and the areas where substantially no radiation or less than a specified dose should be delivered (e.g., sensitive structures including the bowels, optic nerves, spinal cord, and the like). In some embodiments, when determining the treatment plan, TPC 26 may also consider a set of "machine constraints," which detail the nature of the apparatus including, for example, the geometry of the beam and the collimators, maximum dose rates, maximum rotation speeds of the gantry, or the like, or a combination thereof. TPC 26 may then apply an algorithm to produce a treatment plan comprising detailed instructions for the radiotherapy apparatus in terms of required rotation speeds, dose rates, MLC shapes, etc., and their variation with time.

Imaging radiation source 24 and imaging device 30 (referred to as imaging acquisition device collectively) are configured to capture one or more images of the patient's anatomy. Imaging radiation source 24 is configured to generate imaging radiation beam 28 towards the isocenter 14 so that imaging radiation beam 28 may pass through patient 12 and be detected by imaging device 30. The imaging source 24 may be located in a known position relative to therapy radiation source 16, so that the images of the patients anatomy and the target region 15 acquired by imaging device 30 can be correlated with the radiation emitted by therapy radiation source 16. In some embodiments, imaging device 30 may be arranged to rotate with imaging radiation source 24 and fixedly spaced directly opposite, at 180 degrees.

Therapy radiation source 16 and collimator set 20, the imaging source 24 and the imaging device 30 and their respective control and movement mechanisms (not shown) are all operatively connected to TPC 26, which may be also connected to other data processing and/or storage devices (not shown) if these are required to assist TPC 26 and to a user interface such as a computer and linked display (not shown) for the operator to control the system so as to deliver the prescribed dose to the target region.

In practice, an image (which is preferably a three-dimensional image, obtained by, e.g., acquiring a succession of different images of the target region from different angles) is first acquired of target region 15 (though patient tissue surrounding that region will often also be imaged, so that the effects of radiation on that surrounding or adjacent, non-target tissue can be controlled and the radiation delivered thereto can be limited to whatever level is appropriate (which may be nil in the case of critically sensitive tissues or organs, or some level above that but below the level to be delivered to the target region for other, less-sensitive tissues). This image may then be fed into TPC 26. In order to reduce the dose to non-targeted organs during radiotherapy, system 100 may image the region of the body to be treated as close to the time of treatment as possible. However, in practice, the image may be acquired in advance and may use some other imaging system than imaging radiation source 24. In some embodiments, imaging radiation source 24 and imaging device 30 may be in the form of an imaging device comprises a magnetic resonance image (MRI) device, a cone-beam computed tomography (CBCT) scanner, an ultrasonic device, an electronic portal imaging device (EPID).

Figure 2:
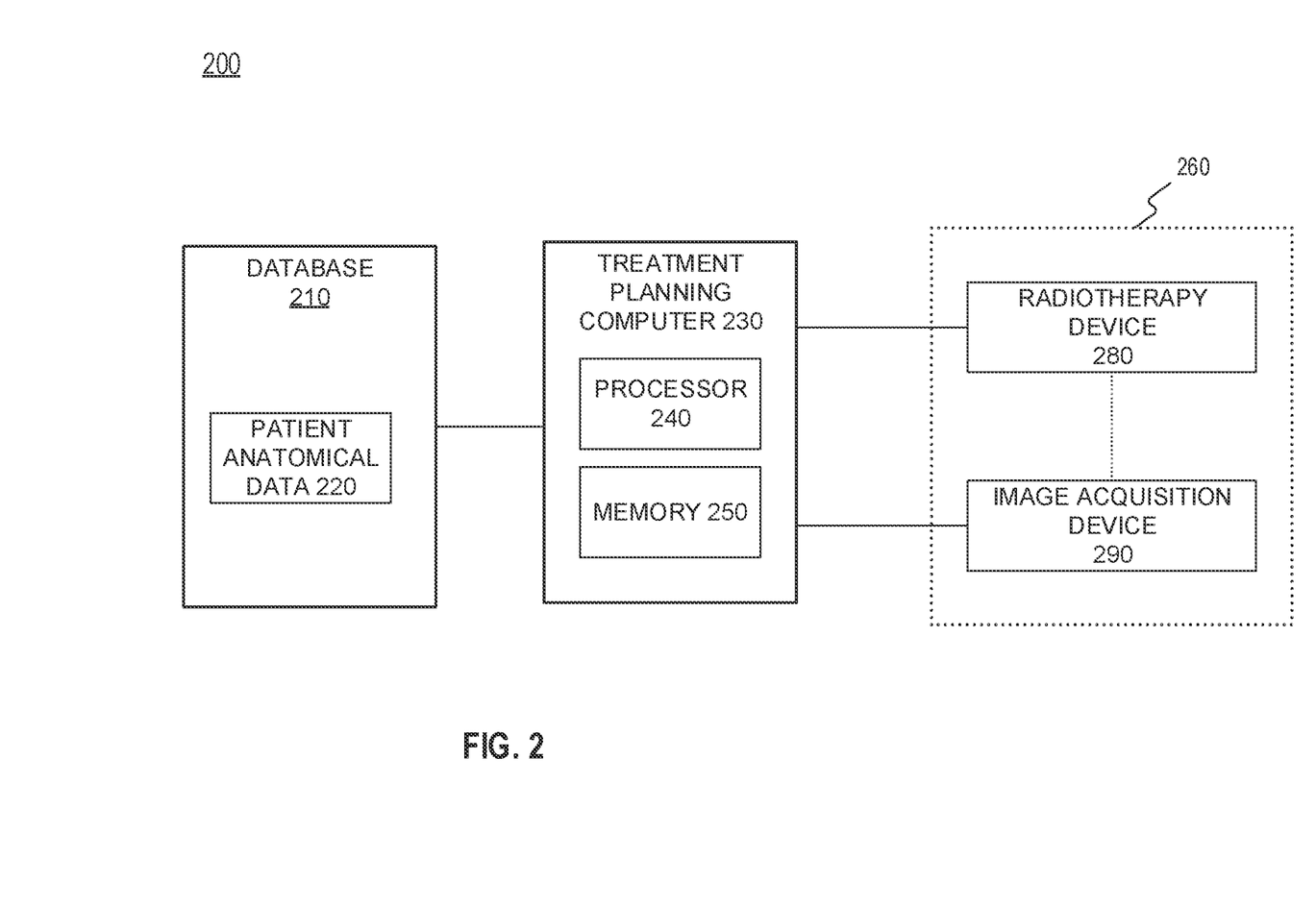
FIG. 2 is a block diagram of an exemplary radiotherapy system, consistent with disclosed embodiments, consistent with disclosed embodiments.

FIG. 2 illustrates an exemplary radiotherapy system for generating a radiation therapy treatment plan or updating an existing radiation therapy treatment plan. Radiotherapy system 200 may be an embodiment of radiotherapy system 100. Radiotherapy system 200 includes a treatment planning computer (TPC) 230, a database 210, a radiotherapy device 280, and an imaging acquisition device 290.

TPC 230 may be an embodiment of TPC 26 shown in FIG. 1 and described above. For example, TPC 230 may generate and store radiation therapy treatment plans for a particular patient to be treated, radiation therapy treatment plans for other patients, as well as other radiotherapy information (e.g., beam angles, dose-histogram-volume information, the number of radiation beams to be used during therapy, the beam angles, the dose per beam, and the like). As another example, TPC 230 may provide information about a particular radiation dose to be applied to the patient and other radiotherapy related information.

TPC 230 may include a processor 240 and a memory 250. Processor 240 may be configured to perform the functions of TPC 230 disclosed herein. Processor 240 may include one or more general-purpose processing devices such as a microprocessor, a central processing unit (CPU), a graphics processing unit (GPU), an accelerated processing unit (APU), or the like. In some embodiments, processor 240 may be a complex instruction set computing (CISC) microprocessor, a reduced instruction set computing (RISC) microprocessor, a very long instruction Word (VLIW) microprocessor, a processor implementing other instruction sets, or processors implementing a combination of instruction sets. Processor 240 may also be one or more special-purpose processing devices such as an application specific integrated circuit (ASIC), a field programmable gate array (FPGA), a digital signal processor (DSP), a System on a Chip (SoC), or the like. As would be appreciated by those skilled in the art, in some embodiments, processor 240 may be a special-purpose processor, rather than a general-purpose processor. Processor 240 may include one or more known processing devices, such as a microprocessor from the Pentium™, Core™, Xeon™, or Itanium® family manufactured by Intel™, the Turion™, Athlon™, Sempron™, Opteron™, FX™, Phenom™ family manufactured by AMD™, or any of various processors manufactured by Sun Microsystems. Processor 240 may also include graphics processing units such as a GPU from the GeForce®, Quadro®, Tesla® family manufactured by Nvidia™, GMA, Iris™ family manufactured by Intel™, or the Radeon™ family manufactured by AMD™. Processor 240 may also include accelerated processing units such as the Desktop A-4 (6, 8) Series manufactured by AMD™, the Xeon Phi™ family manufactured by Intel™. The disclosed embodiments are not limited to any type of processor(s) or processor circuits otherwise configured to meet the computing demands of identifying, analyzing, maintaining, generating, and/or providing large amounts of imaging data or manipulating such imaging data to localize and track a target or to manipulate any other type of data consistent with the disclosed embodiments. In addition, the term "processor" or processor circuit may include more than one processor, for example, a multi-core design or a plurality of processors each having a multi-core design. Processor 240 can execute sequences of computer program instructions, stored in memory 250, to perform various operations, processes, methods that will be explained in greater detail below.

Memory 250 may be configured to store data for the components of radiotherapy system 200. For example, memory 250 may store image data (e.g., 3D MRI, 4D MRI, 2D slices, etc.) received from image acquisition device 290. Memory 250 may also store any other type of data/information in any format that the radiotherapy system 200 may use to perform operations consistent with the disclosed embodiments. Memory 250 may include a read-only memory (ROM), a flash memory, a random-access memory (RAM), a dynamic random-access memory (DRAM) such as synchronous DRAM (SDRAM) or Rambus DRAM, a static memory (e.g., flash memory, static random access memory), etc., on which computer executable instructions are stored in any format. The computer program instructions can be accessed by processor 240, read from the ROM, or any other suitable memory location, and loaded into the RAM for execution by processor 240. For example, memory 250 may store one or more software applications. Software applications stored in memory 250 may include, for example, an operating system for common computer systems as well as for software-controlled devices. Further, memory 250 may store an entire software application or only a part of a software application that is executable by processor 240. For example, memory 250 may store one or more radiation therapy treatment plans generated by TPC 230. In addition, memory 250 may store a plurality of software modules.

In some embodiments, memory 250 may include a machine-readable storage medium. While the machine-readable storage medium in an embodiment may be a single medium, the term "machine-readable storage medium" should be taken to include a single medium or multiple media (e.g., a centralized or distributed database, and/or associated caches and servers) that store the one or more sets of computer-executable instructions or data. The term "machine-readable storage medium" shall also be taken to include any medium that is capable of storing or encoding a set of instructions for execution by the machine and that cause the machine to perform any one or more of the methodologies of the present disclosure. The term "machine-readable storage medium" shall accordingly be taken to include, but not be limited to, solid-state memories, optical and magnetic media.

In an embodiment, memory 250 may be configured to store at least the following types of data: Digital Imaging and Communications in Medicine (DICOM) data, dosage data, optimization parameters, jaw position data, beamlet data, segment data, segment shapes, voxel dose distribution data, initial dose data, and dose-volume histogram (DVH) data, image data.

TPC 230 (e.g., via processor 240) may be communicatively coupled to memory 250, and processor 240 may be configured to execute executable computer instructions stored in memory 250. For example, processor 240 may execute one or more treatment plans to implement functionalities of radiotherapy system 200 disclosed herein. TPC 230 may communicate with database 210. Database 210 may include patient anatomical data 220. Patient anatomical data 220 may include anatomical data determined according to one or more images of a patient acquired by imaging acquisition device 290. Database 210 may include relational databases such as Oracle™ databases, Sybase™ databases, or others and may include non-relational databases, such as Hadoop sequence files, HBase, Cassandra, or others. Such remote programs may include, for example, oncology information system (OIS) software or treatment planning software. In some embodiments, treatment planning software, for example, may be stored on database 210. In some embodiments, database 210 may be located remotely from TPC 230, radiotherapy device 280, and/or imaging acquisition device 290. In some embodiments, database 210 may be integrated with TPC 230. Database 210 may include computing components (e.g., database management system, database server, etc.) configured to receive and process requests for data stored in memory devices of database 210 and to provide data from database 210. One skilled in the art would appreciate that database 210 may include a plurality of devices located either in a central or distributed manner.

In some embodiments, TPC 230 and/or radiotherapy device 280 may communicate with database 210 to send/receive a plurality of various types of data stored on database 210. For example, in some embodiments, database 210 may be configured to store a plurality of images (e.g., 3D MRI, 4D MRI, 2D MRI slice images, CT images, ultrasound images, 2D Fluoroscopy images, X-ray images, raw data from MR scans or CT scans, Digital Imaging and Communications in Medicine (DICOM) data, etc.) from image acquisition device 280.

Radiotherapy device 280 may be an embodiment of therapy radiation source 16 illustrated in FIG. 1 and described above. For example, radiotherapy device 280 may be configured to emit therapy radiation beam when rotatable gantry 18 rotates along a trajectory.

Image acquisition device 290 may be an embodiment of imaging radiation source 24 and imaging device 30. Imaging acquisition device 290 may be configured to acquire medical images (e.g., Magnetic Resonance Imaging (MRI) images, 3D MRI, 2D streaming MRI, 4D volumetric MRI, Computed Tomography (CT) images, Cone-Beam CT, Positron Emission Tomography (PET) images, functional MRI images (e.g., fMRI, DCE-MRI and diffusion MRI), X-ray images, fluoroscopic image, ultrasound images, radiotherapy portal images, single-photo emission computed tomography (SPECT) images, and the like) of the patient. In some embodiments, image acquisition device 280 may be an MRI imaging device, a CT imaging device, a PET imaging device, an ultrasound device, a fluoroscopic device, a SPECT imaging device, or other medical imaging device for obtaining one or more medical images of the patient. Images acquired by imaging acquisition device 290 can be stored within database 210 as either imaging data and/or test data. By way of example, the images acquired by imaging acquisition device 290 may also be stored by radiotherapy device 280 in memory 250. In some embodiments, image acquisition device 290 may be integrated with radiotherapy device 280 as a single apparatus (e.g., an MRI device combined with a linear accelerator, also referred to as an MRI-Linac).

In some embodiments, image acquisition device 290 may be configured to acquire one or more images of the patients anatomy for a region of interest (e.g., a target organ, a target tumor or both). The one or more images may include a plurality of 2D slices. Alternatively or additionally, the one or more images may include one or more 3D MRI images captured in real-time (or substantially in real-time). Each 2D slice can include one or more parameters (e.g., a 2D slice thickness, an orientation, and a location, etc.). The one or more parameters can be adjusted by using processor 240, to include the target. For instance, selected features of the 2D slice can be manipulated, e.g., by adjusting the magnetic field gradient or radio frequency (RF) waveform properties. For example, the position of the slice can be varied by changing the modulation frequency of the RF pulse and maintaining the same gradient strength. Further, the orientation of the slice can be varied, for example, by using a physically different gradient axis (e.g., the selected slice can be orthogonal to the gradient applied). In some embodiments, image acquisition device 290 may acquire a 2D slice in any orientation. For example, an orientation of the 2D slice can include a sagittal orientation, a coronal orientation, an axial orientation, or an oblique orientation. In addition, these orientations, for example, can correspond to a magnetic field gradient (e.g., Gx, Gy, or Gz, respectively) associated with the MRI or the MRI-Linac. In an example, 2D slices can be determined from information such as a 3D MRI volume. Such 2D slices can be acquired by image acquisition device 290 in real-time (or substantial in real-time) while a patient is undergoing radiation therapy treatment, for example, when using the radiotherapy device 280. In an embodiment, the 2D image slices can be provided by an ultrasound device as an image acquisition device 280.

Figure 3:
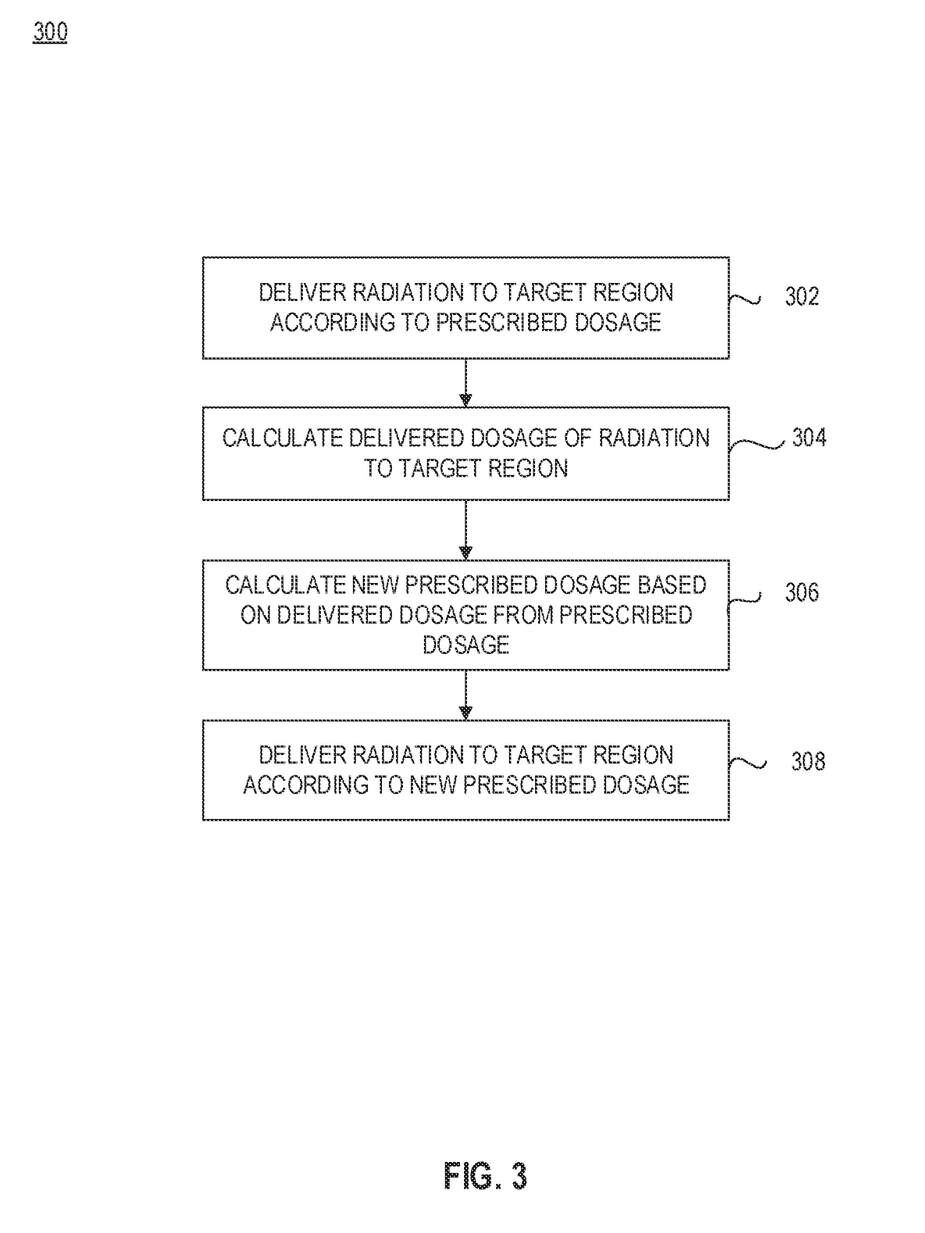
FIG. 3 is a flowchart of an exemplary process for delivering radiation to a target region, consistent with disclosed embodiments.

FIG. 3 is a flowchart of an exemplary process for delivering radiation to a target region. Process 300 may be performed by radiotherapy system 200.

In step 302, radiation may be delivered to a target region according to a prescribed dose. TPC 230 may determine a prescribed dose. Radiation delivery typically involves several discrete fractions. For example, a treatment plan may be divided into six fractions, and the patient may receive one fraction every day for six days. In some embodiments, the prescribed dose may include the dose of radiation for one of the fractions to be delivered. For instance, TPC 230 may determine the prescribed dose according to the total dose of the fractions and the dose of fraction(s) that has been delivered (if any). TPC 230 may also generate a treatment plan according to the prescribed dose. For example, TPC 230 may determine a plurality of control points of an arc. Each of the control points may define a position of rotatable gantry 18, the dose that is to be delivered between this and the next (or previous) control point, and the shape of the collimator set 20 at that control point. In some embodiments, each control point may correspond to a beam angle. TPC 230 may also obtain one or more images of the patients anatomy (e.g., around the target region) and determine the anatomical data of the patient. Additionally, TPC 230 may determine ideal dose distribution based on the prescribed dose and the anatomical data. TPC 230 may also perform a fluence optimization process and beam angle segmentation process. TPC 230 may further set the parameters for each of the control points. TPC may cause radiotherapy system 100 to deliver the arc radiation to the target region based on the treatment plan.

In step 304, the delivered dose of radiation to the target region may be calculated. For example, TPC 230 may directly use the radiation dose to be delivered to the target region as the delivered dose. Alternatively, radiotherapy system 200 may include a detector (not shown in FIG. 1 or 2) placed opposite to therapy radiation source 16. The detector may be configured to detect the radiation delivered to the patient and/or the target region. In some embodiments, the detector may include an image device configured to acquire one or more images of the patient and/or the target region, and TPC 230 may determine the delivered dose to the target region based on the acquired image(s).

In step 306, the prescribed dose may be updated based on a bias dose (also referred to herein as the delivered dose) in this arc treatment. TPC 230 may update the prescribed dose according to the dose delivered to the target region. For example, TPC 230 may subtract the dose delivered in the arc treatment from the previous prescribed dose. By way of example, for a multi-fraction treatment, a dose may be delivered to the patient in day one, and the delivered dose in day one may be determined and used for the optimization of subsequent fraction treatment(s). For instance, if a voxel has a prescribed dose of 10 Gy, TPC 230 may subtract a bias dose of 3 Gy that has been delivered in day one from the prescribed dose (i.e., resulting an updated dose of 7 Gy) in the optimization of the subsequent treatment(s). As another example, for a fraction treatment, a dose may be delivered to the patient in the first sub-fraction treatment, TPC 230 may determine a bias dose of the first sub-fraction treatment. TPC 230 may update the prescribed dose for the subsequent sub-fraction treatment(s) based on the bias dose.

In some embodiments, TPC 230 may determine a bias dose of a fraction treatment (or a sub-fraction treatment) based on the planned dose (assuming the planned dose would be delivered to the patient accordingly). Alternatively, TPC 230 may determine the bias dose based on imaging information and/or real-time linac parameters obtained by TPC 230 during or after the treatment. For example, imaging acquisition device 290 may capture an image depicting updated anatomical data of the patient. TPC 230 may receive the image and determine the updated anatomical data based on the image. TPC 230 may also determine a bias dose based on the updated anatomical data and various linac parameters.

In step 308, radiation may be delivered to the target region according to the updated prescribed dose. For example, TPC 230 may update the treatment plan (or generate a new treatment plan) according to the updated prescribed dose. This step is similar to step 302, and for brevity, similar descriptions for step 308 are not repeated in detail here. TPC 230 may terminate the treatment if a condition for the termination is satisfied. For example, TPC 230 may terminate the treatment after a predetermined number of arc treatments has been delivered.

Figure 4:
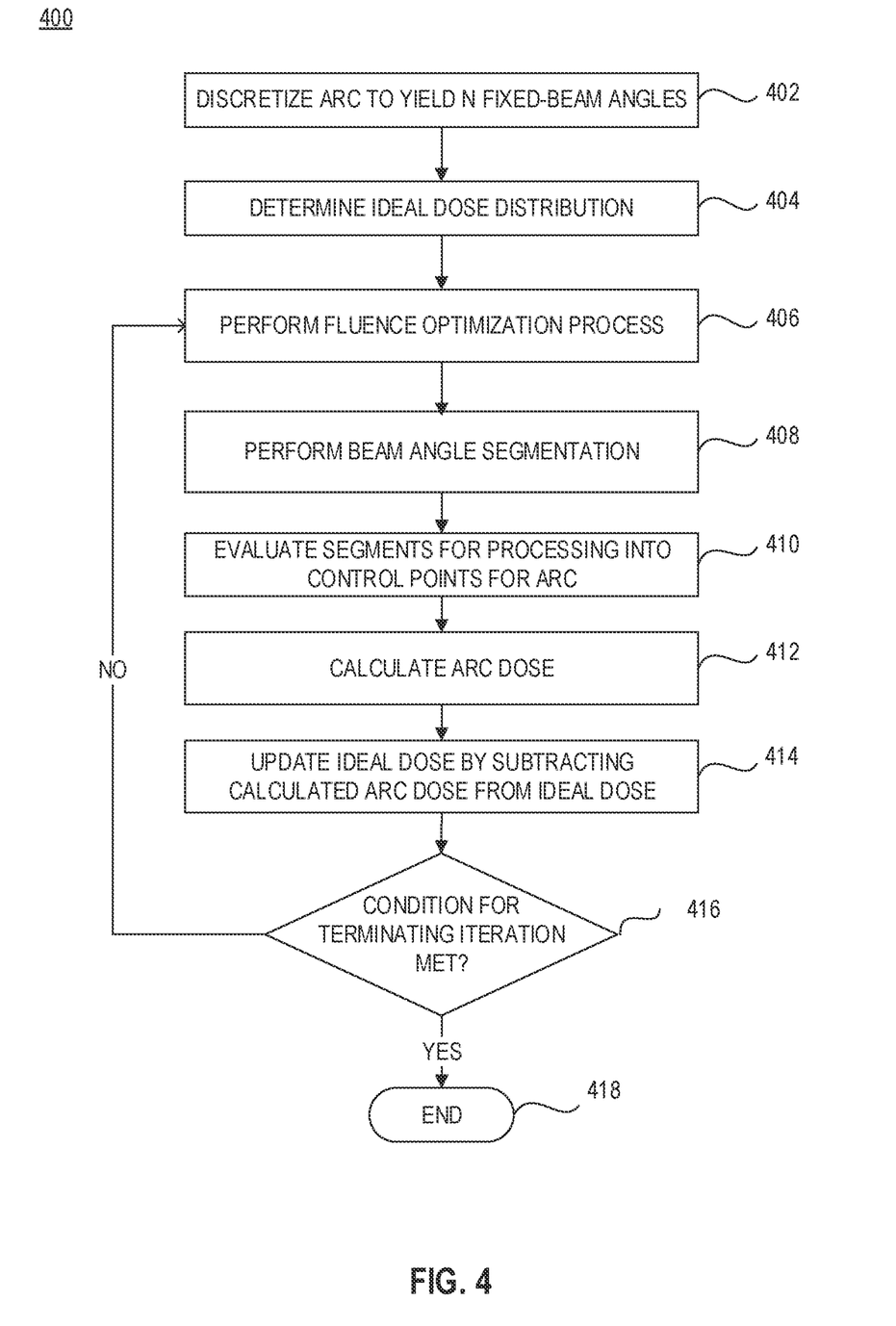
FIG. 4 is a flowchart of an exemplary process for delivering the prescribed dose of radiation, consistent with disclosed embodiments.

FIG. 4 is a flowchart of an exemplary process for delivering the prescribed dose of radiation. Process 400 may be an embodiment of process 300 illustrated in FIG. 3. Process 400 may be performed in each of fractions of a prescribed dose. Alternatively, process 400 may be performed in some of fractions of a prescribed dose.

In step 402, an arc of arc treatments may be discretized into a plurality of beam angles. In an arc treatment, rotatable gantry 18 may rotate along an arc, and therapy radiation source 16 may emit therapy radiation beam 22 when rotatable gantry 18 rotates. The arc may be a single 360-degree circle or a portion thereof (e.g., 180 degrees). By way of example, TPC 230 may divide the circle into 3 discrete increments, each yielding 120 discrete beam angles. In some embodiments, the beam angles may be uniformly spaced. Alternatively, the beam angles may be unevenly spaced. Each beam angle may correspond to a control point, which may define a position of rotatable gantry 18, the dose that is to be delivered between this and the next (or previous) control point, and the shape of the collimator set 20 at that control point.

In some embodiments, step 402 may be performed once for all fractions of a prescribed dose. For example, TPC 230 may determine an arc and a plurality of beam angles for the first fraction and save the information into a storage device. In a subsequent fraction treatment, TPC 230 may obtain the information and use the determined arc and beam angles for this subsequent fraction treatment. In this example, TPC 230 may skip step 402 for one or more subsequent fraction treatments.

In step 404, ideal dose distribution may be determined. TPC 230 may determine an ideal dose distribution for each beam angle based on the prescribed dose. Alternatively or additionally, TPC 230 may determine an ideal dose distribution for each beam angle based on the daily (or current) patient anatomy. For example, TPC 230 may decompose each beam into a matrix of beamlets (e.g., pencil beams). By way of example, a beamlet may be $3 \times 10$ mm$^2$ or $3 \times 5$ mm$^2$. The prescribed dose used for determining the ideal dose distribution may be the originally prescribed dose. Alternatively, the prescribed dose may be an updated prescribed dose determined according to the radiation delivered in previous fraction treatment(s).

In step 406, a fluence optimization process for each beam angle may be performed. For example, TPC 230 may perform a fluence optimization process for each beam angle based on the beamlet data and the anatomical data of the patient and the target region. As a result, TPC 230 may generate a distribution for a sub-dose to be delivered at that beam angle (and the corresponding control point), the separate sub-doses from all the angles in combination substantially equaling the ideal dose.

In some embodiments, the anatomical data of the patient and the target region may be determined based on one or more images acquired by imaging acquisition device 290 before the fractional treatment begins or in real time. For example, imaging acquisition device 290 may acquire one or more images of the anatomy of the patient and the target region before the radiation treatment begins (also referred to as inter-fractional image). TPC 230 may determine the anatomical data of the patient and the target region according to the acquired image(s). TPC 230 may also use the anatomical data for all fluence optimization processes performed in step 406 (and/or in the iteration process comprising step 406). Alternatively, imaging acquisition device 290 may acquire one or more images of the anatomy of the patient and the target region before the radiation treatment begins and during the fractional treatment (also referred to as infra-fractional image). TPC 230 may determine inter-fractional and intra-fractional anatomical data of the patient and the target region based on the acquired images. TPC 230 may also use the (inter-fractional and intra-fraction) anatomical data for all fluence optimization processes performed in step 406 (and/or in the iteration process comprising step 406). In some embodiments, one or more inter-fractional (or intra-fractional) movements may be registered in the imaging step prior to the next fractional treatment (or a sub-fractional treatment), the treatment plan for the next fraction (or the sub-fractional treatment) is likely to differ from the previous treatment plan, in terms of at least one of the beam angles, beam-angle-optimisation, fluence optimisation and segmentation. These differences, over several fractional treatments (or sub-fractional treatments), are able cumulatively to take account of those factors which led to the undelivered dose in one or more preceding fractions (or sub-fractional treatments). This improves the efficiency of treatment for a patient as, instead of painstakingly and time-consumingly trying to complete the last elements of undelivered dose during one fractional treatment, the undelivered dose from that fraction can be factored into the next fractional treatment, and/or into subsequent fractional treatments (or subsequent sub-fractional treatments).

In step 408, beam angle segmentation may be performed. For example, TPC 230 may segment each sub-dose distribution profile into segments, each segment comprising a plurality of pencil beams of matching fluence.

In step 410, the segments may be evaluated for processing into control points of the arc. For example, TPC 230 may split the beam's fluence into a plurality of discrete intensity levels (e.g., 1000 levels). Each pencil beam may be given an intensity value between 0-1000. The pencil beams are then grouped into segments based on their location and intensity level, and whether or not they would be physically deliverable by radiotherapy system 200. TPC may select one of the determined segments based on a selection metric. The selection metric may be determined based on the size of the segment, the shape of the segment, and/or the level of intensity of the segment.

In some embodiments, the selection metric may relate to the efficiency of a segment. For example, TPC 230 may determine the efficiency of each segment. In some embodiments, the efficiency of a segment is determined according to the result of the multiplication between the segments area and its intensity level—however different objective functions could be used to describe the efficiency of each segment. Merely by way of example, a fluence optimization map includes a 7×5 grid having 35 cells. Each cell corresponds to a pencil beam and indicates the radiation dose to be delivered to the target region thereby. Assume there is a first group of 4 cells towards the centre of the grid, each of which has a fluence of 10 Gy, a second group of 3 cells in a line along the top edge of the grid each of which has a fluence of 7 Gy, and a third group of 6 cells to the right hand side of the grid, each of which has a fluence of 4 Gy. Using the above calculation, the efficiency of the first group is 40, in the second group 21, and of the third group 24. TPC 230 may select the segment of the first group based on its highest efficiencies among the groups. Alternatively, a predetermined fluence level of 7 could be applied, and a group formed of all those contiguous cells having a fluence equal to or greater than 7. Because a fluence level has been predetermined in forming this group, its efficiency will be the predetermined fluence level (or segment intensity) multiplied by the area (i.e., the number of cells in the group). Other groups of "matched" fluence would then be formed (using either of the above-described methods), and then the groups ranked in order of efficiency as described. Alternatively, TPC 230 may determine the efficiency of a segment based on an average fluence level of the cells in the segment.

In some embodiments, TPC 230 may also determine segments based on the constraints of radiotherapy system 200. The constraints may include mechanical and therapeutical constraints, including, for example, the moving speed of leaves of the collimators between two control points, maximum or minimum dose rates, maximum rotation speeds of the gantry, or the like, or a combination thereof. For example, in a VMAT system, the dose rate variation between neighboring angles can be constrained within a certain range. Merely by way of example, therapy radiation source 16 emits beams and collimator set 20 changes the shape as rotatable gantry 18 rotates. Given the maximum speed of rotatable gantry 18 rotates, collimator set 20 (e.g., jaw and/or MCL) may not be able to change the shape to a desired shape at the next control point between the elapsed time between two control points. Similarly, the monitor unit (MU) of radiation delivered to the target region for the arc segment may not be high enough to reach a desired level between the elapsed time between two control points or may be higher than an allowed level. In other words, a segment may be non-deliverable because of these constraints, or other segments may have to be adjusted to compensate this segment, which may lead to inefficient treatments. TPC 230 may replace a non-deliverable segment with another segment for that beam angle. In some embodiments, TPC 230 may determine one or more non-deliverable segments violating a constraint of the radiotherapeutic apparatus. For example, the constraint may relate to when a gantry rotates at a predetermined speed (e.g., the maximum speed) or the leaves of the MLC move between two control points at the maximum speed. TPC 230 may also replace the non-deliverable segment(s) with a segment that does not violate a mechanical or efficiency constraint of the radiotherapeutic apparatus. More description of updating a non-deliverable segment can be found in FIG. 6 and the description thereof.

TPC 230 may also cause radiotherapy system 200 to deliver radiation of the arc treatment according to the determined segments. For example, TPC 230 may configure the parameters for the control points (e.g., a set of MLC leaf positions, MLC shape, jaw positions, gantry rotation speed, gantry position, dose rate, and/or any other parameters). Radiotherapy system 200 may deliver the arc treatment accordingly.

In step 412, the arc dose may be calculated. For example, TPC 230 may determine the arc dose delivered to the target region based on the dose delivered in the arc treatment and the anatomical data of the patient and the target region. In some embodiments, TPC 230 may further perform an arc/segment weight optimization (ASWO) on the dose of each segment, which may adjust the arc segment MUs to fully converge to the original prescribed dose. For example, for a set of segments arranged in one or more gantry angles along with the corresponding prescribed MUs that collectively deliver a 3D dose, TPC 230 may perform an optimization method to optimize the dose that each segment delivers thereby adjusting the individual segment MUs to better match the goal dose distribution.

In step 414, the ideal dose may be updated based on the arc dose. For example, TPC 230 may update the ideal dose by subtracting the determined arc dose from the prescribed dose. Alternatively, TPC 230 may update the ideal dose according to a bias dose algorithm based on the prescribed dose and the arc dose. In some embodiments, TPC 230 may further perform an arc/segment weight optimization (ASWO) on the dose of each segment, which may adjust the arc segment MUs to fully converge to the original prescribed dose. For example, for a set of segments arranged in one or more gantry angles along with the corresponding prescribed MUs that collectively deliver a 3D dose, TPC 230 may perform an optimization method to optimize the dose that each segment delivers thereby adjusting the individual segment MUs to better match the goal dose distribution. In some embodiments, the optimization may be performed at the end of the optimization process in treatment planning as a post-processing step.

In step 416, the condition for terminating the iteration process may be determined. If the condition is met, process 400 may end, and the treatment may be terminated. For example, the condition for terminating the treatment may be that a predetermined number of arc treatments have been delivered. Alternatively or additionally, the condition may be that the updated ideal dose is less than or equal to a threshold dose. In some aspects, the condition for terminating the treatment may include Organ at Risk (OAR) constraints, such as an OAR threshold. For example, TPC 230 may be configured to deliver greater than the ideal dose as long as OAR constraints are met. If TPC 230 determines that the condition is met, TPC 230 may cause radiotherapy system 200 to terminate the treatment at step 418.

On the other hand, if the condition is not met, process 400 may proceed to 406, and steps 406-416 may be repeated.

Figure 5:
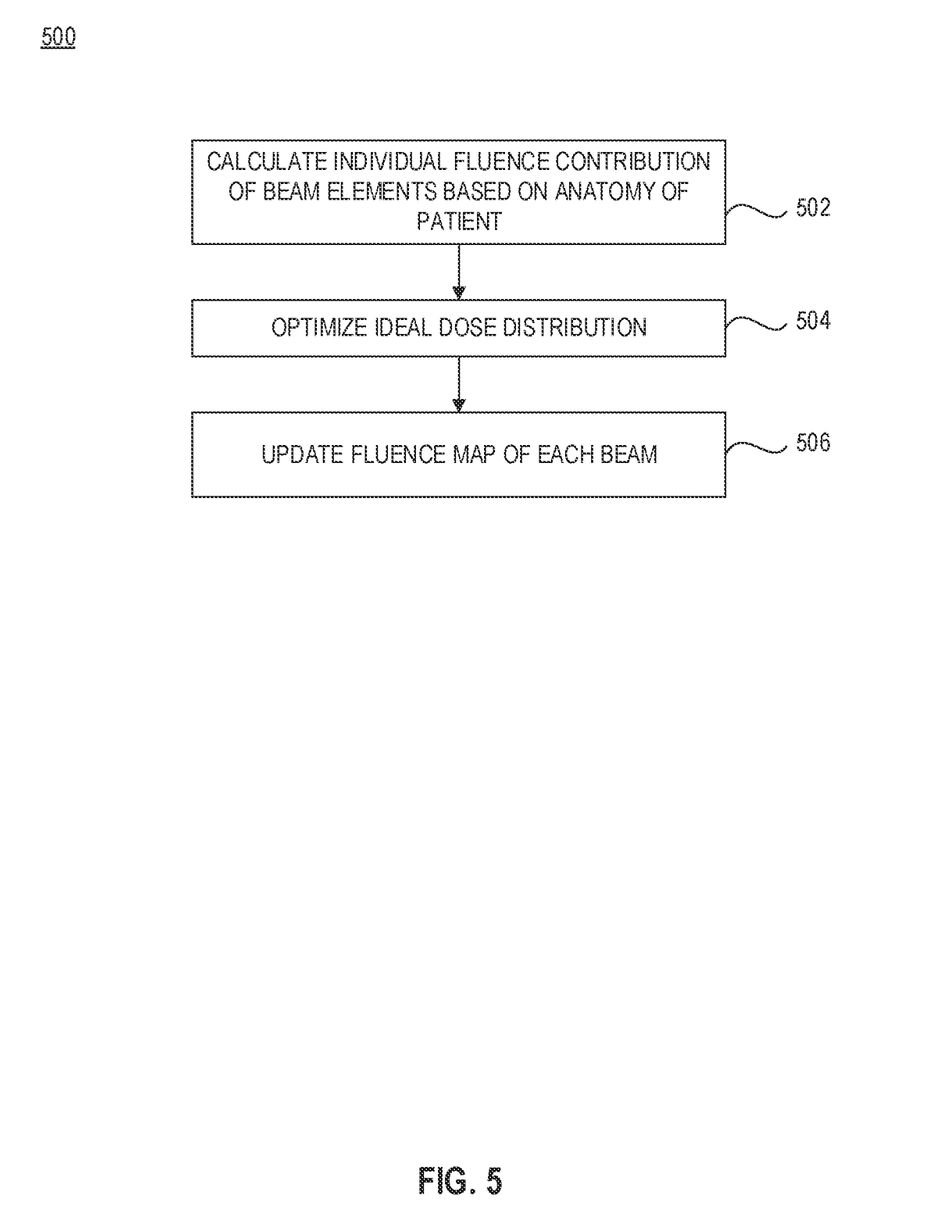
FIG. 5 is a flowchart of an exemplary process for optimizing fluence, consistent with disclosed embodiments.

FIG. 5 is a flowchart of an exemplary process for optimizing fluence. In some embodiments, step 406 of process 400 illustrated in FIG. 4 may be performed based on process 500.

In step 502, the individual fluence contribution of beam elements may be calculated. For example, TPC may calculate the 3D dose fluence of individual beamlets that go through the target region. By way of example, after determining the individual beam angles (and corresponding control points), TPC 230 may define a mask that outlines a beam to be delivered from each beam angle. The mask of a beam corresponds to the outline of the target region in the current patients anatomy (or the latest anatomy of the patient available) as seen from that beam angle (or the arc segment corresponding to the beam angle). The TPC may also determine the sub-dose of radiation to be delivered at each beam angle (where the combined sub-doses from every beam angle add up to, or approach but do not exceed, the prescribed dose distribution).

In step 504, ideal dose distribution for each beam angle may be optimized. For example, TPC may optimize the weights of individual fluence contribution of beam elements so that the beam elements collectively deliver a 3D dose as close as possible to (or better matching with) the remaining ideal dose to the target region. In some embodiments, the ideal dose distribution for each beam angle may be optimized using an inverse dose optimization algorithm. For example, the algorithm may take clinical constraints into account in optimizing the idea dose distribution. TPC 230 may generate a plurality of hypothetical beamlets (e.g., pencil beams). The beamlets may be straight-line pathways, which may have a conical or cylindrical shape, with a very small cross-sectional area. The pencil beams may be generated according to a process based on the Monte Carlo method, the collapsed cone method, or any other suitable discretizing engine. TPC 230 may perform a fluence optimization process on the pencil beams using the pencil beam data from the discretization process and anatomical data of the patient and the target region from the image.

For the beams having been discretized into pencil beams, fluence optimization may be performed. Any known fluence optimization implementation may be used. In some embodiments, the faster fluence optimization implementations are preferred for the iterative process. The fluence optimization may be performed using the pencil beam data from the discretization process and anatomical data of the patient and the target region from the image. The goal of the fluence optimization is to optimize the remaining dose to be delivered in an iteration. In some embodiments, the anatomical data of the patient and the target region may be derived from the current patient's anatomy (or the latest anatomy data of the patient available). As a result, TPC 230 may generate a distribution for a sub-dose to be delivered at that beam angle (and the corresponding control point), the separate sub-doses from all the angles in combination substantially equaling the ideal dose.

In some embodiments, the anatomical data of the patient and target region may be determined based on one or more images acquired by imaging acquisition device 290. For example, imaging acquisition device 290 may acquire an image of the anatomy of the patient and target region before TPC 230 performs the optimization process. TPC 230 may determine the anatomical data of the patient and the target region based on the obtained image. In some embodiments, because there is likely to be inter-fractional movement in the majority of cases, one or more inter-fractional movements may be registered in the imaging step before the next fractional treatment. TPC 230 may determine the anatomical data of the patient and target region based on the obtained image and the registered inter-fractional movement(s). In some embodiments, imaging acquisition device 290 may acquire an image (or a set of images) for one fraction treatment, and TPC 230 may determine anatomical data once for the fraction treatment. Alternatively, imaging acquisition device 290 may acquire a plurality of images for one fraction treatment. For example, imaging acquisition device 290 acquires an image (or an updated image) for every arc treatment, and TPC 230 determines the anatomical data of the patient and the target region for every arc treatment. TPC 230 may also perform a fluence optimization process after determining updated anatomical data. Alternatively, imaging acquisition device 290 acquires an image for a number of arc treatments (e.g., acquiring an image once two arc treatments), and TPC 230 determines the anatomical data and performs a fluence optimization at the same frequency.

In some embodiments, a bias dose may be determined based on the planned dose (assuming the planned dose would be delivered to the patient accordingly). Alternatively, TPC 230 may determine the bias dose based on imaging information and/or real-time linac parameters obtained by TPC 230 during or after the treatment. For example, imaging acquisition device 290 may capture an image depicting updated anatomical data of the patient. TPC 230 may receive the image and determine the updated anatomical data based on the image. TPC 230 may also determine a bias dose based on the updated anatomical data and various linac parameters. TPC 230 may also perform a fluence optimization process to generate a distribution profile for a sub-dose to be delivered for each of the plurality of arc segments based on the bias dose and the prescribed dose. For example, TPC 230 may acquire an image depicting updated anatomical data of the patient (also referred to herein as the updated image) during an infra-fraction treatment and after a certain amount of the prescribed dose has been delivered to the target region. TPC 230 may also determine a bias dose based on the dose that has been delivered to the target region (or the whole anatomy including target region(s) and OARs). TPC 230 may further reconstruct the dose for the remaining treatment based on the bias dose. In some embodiments, TPC 230 may also perform a fluence optimization process based on the bias dose similar to the optimization process described elsewhere in this application. In some embodiments, in addition to the bias dose, TPC 230 may also take the movement(s) registered in the imaging step prior to capturing the updated image into account when reconstructing the dose for the remaining treatment. In some embodiments, TPC may further configure the delivery parameters of the linac based on the anatomical motion (e.g., identified via the movement(s) registered in the imaging step and/or updated image) for the subsequent treatment(s).

In step 506, the fluence map of each beam may be updated according to the optimization process performed in step 504. For example, TPC 230 may update the fluence map of each beam according to the updated weights of the corresponding beam elements of that beam angle.

Figure 6:
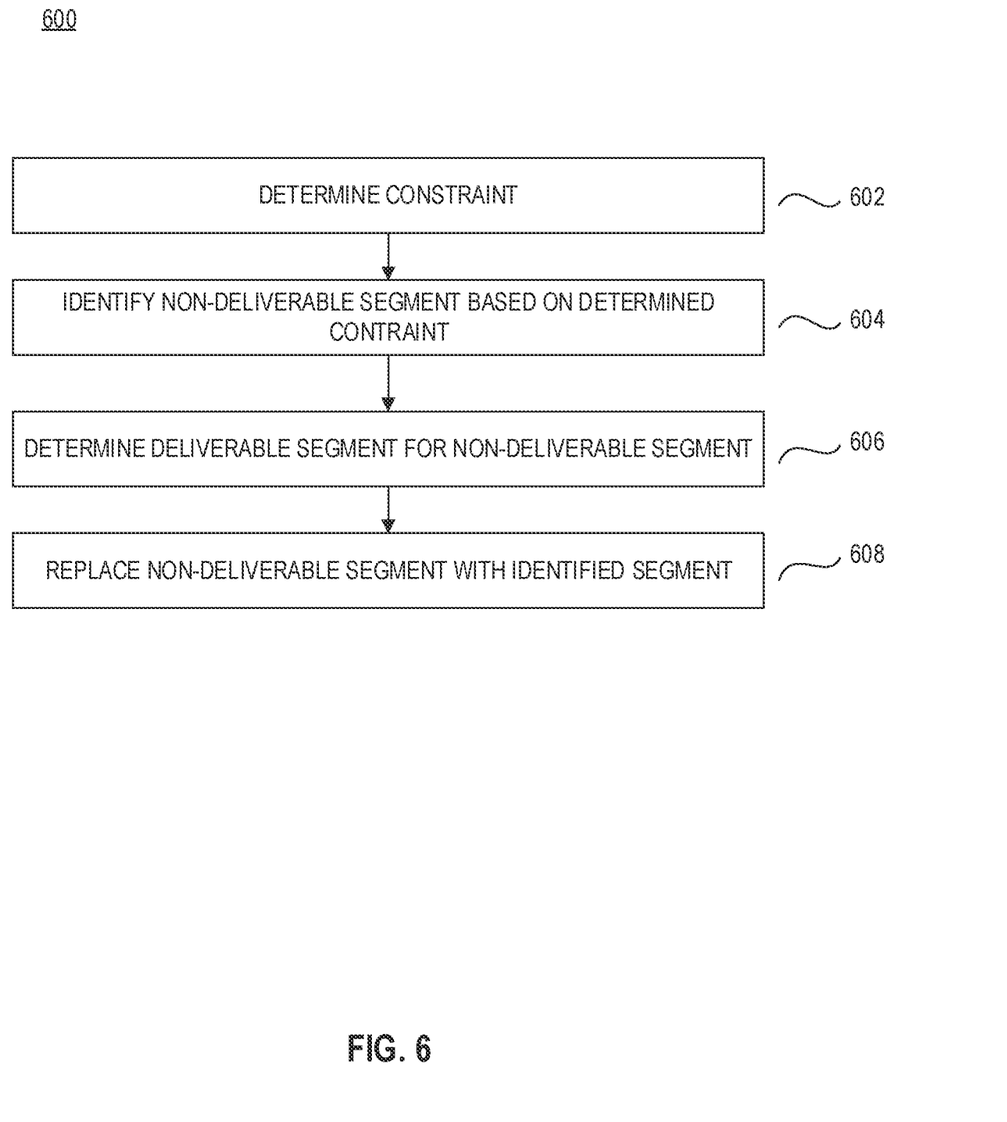
FIG. 6 is a flowchart of an exemplary process for evaluating a segment for processing into a control point, consistent with disclosed embodiments.

FIG. 6 is a flow chart of an exemplary process for evaluating a segment for processing into a control point.

In step 602, one or more constraints of radiotherapy system 200 may be determined. The constraint(s) of radiotherapy system 200 to be determined may include the gantry speed (e.g., the maximum and minimum speeds), the MLC speed (the maximum speeds moving between two control points), the dose rate/MU per control point, or the like, or a combination thereof. For example, TPC 230 may determine for a segment the maximum tolerance of collimator set 20 (e.g., the maximum leaf and/or jaw distances of collimator set 20) with the elapsed time as rotatable gantry 18 moves from one control point to the next control point at a predetermined speed. Alternatively or additionally, TPC 230 may determine the MU value for radiation to be delivered with the elapsed time for the segment when rotatable gantry 18 maintains the predetermined speed. In some embodiments, the predetermined speed at which rotatable gantry 18 rotates may be the maximum speed of rotatable gantry 18 can rotate (e.g., 10 revolutions/min). Alternatively, TPC 230 may determine the rotation speed based on the prescribed dose. For example, rotatable gantry 18 may rotate at a lower speed than the maximum speed for radiation treatments with a large number of monitor units (e.g., high dose, single-fraction stereotactic radiosurgery procedures for brain tumors).

In step 604, one or more non-deliverable segments may be determined based on the determined constraint(s). TPC 230 may determine one or more segments that violate the determined constraint(s) (which are also referred to herein as non-deliverable segments). For example, TPC 230 may determine a segment for which the distance(s) that the leaf and jaw of collimator set 20 are required to travel to form the desired shape at the corresponding control point may exceed the maximum tolerance as rotatable gantry 18 rotates at a predetermined speed (e.g., at the maximum speed). TPC 230 may then determine this segment as a non-deliverable segment. As another example, TPC 230 may determine the MU value, to be delivered in a segment when rotatable gantry 18 maintains the maximum speed (or the MLC reaches the maximum speed or both), is less than the desirable MU. TPC 230 may then determine that this segment is a non-deliverable segment.

In some embodiments, TPC 230 may update the constraint(s) of radiotherapy system 200 if the number of non-deliverable segments is greater than or equal to a threshold number (or a ratio of non-deliverable segments to all segments is greater than or equal to a threshold ratio), and re-determine one or more non-deliverable segments under updated constraint(s).

In step 606, TPC 230 may determine a deliverable segment for each of the identified non-deliverable segment(s). For example, TPC 230 may determine for a non-deliverable segment based on two valid segments. In some embodiments, these two valid segments may be at adjacent beam angles. Alternatively, one of the two valid segments may be before the beam angle of the non-deliverable segment (e.g., immediately before) and the other after the beam angle of the non-deliverable segment (e.g., immediately after). TPC 230 may also determine a shape of a segment (which is the open area formed by the MLC leaves at the corresponding angle) by interpolating the shapes of the valid segments and designate that segment as the deliverable segment for the non-deliverable segment.

In some embodiments, TPC 230 may determine a deliverable segment for each of the identified non-deliverable segment(s) based on a sliding window approach, where the segmentation leads to connected two valid arcs with shapes that gradually move unidirectionally (e.g., left to right delivering the appropriate dose for each angle).

In some embodiments, when determining a deliverable segment for the non-deliverable segment(s), TPC 230 may take the fluence maps into account. For example, TPC 230 may choose a segment of a valid segment at an adjacent angle (immediately before or after) to replace the non-deliverable segment based on the fluence maps of the non-deliverable segment and valid segment(s). In other words, one shape may be used over more than a gantry angle (or control point), which may increase delivery efficiency and decrease the overall modulation of the MLC.

In step 608, TPC 230 may replace the non-deliverable segment(s) with the correspondingly determined deliverable segments. The replaced segments and the originally determined segments that do not violate the constraint(s) may form a fully connected deliverable arc. TPC 230 may further process these segments to the control points as described elsewhere in this disclosure. TPC 230 may also calculate the arc dose based on these segments. TPC 230 may further update the ideal dose based on the arc dose.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

The exemplary disclosed embodiments describe systems and methods for target tracking using a quality indicator during radiation therapy. The foregoing description has been presented for purposes of illustration. It is not exhaustive and is not limited to the precise forms or embodiments disclosed. Modifications and adaptations of the embodiments will be apparent from a consideration of the specification and practice of the disclosed embodiments.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, an apparatus, system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include software code, such as microcode, assembly language code, a higher-level language code, or the like. The various programs or program modules can be created using a variety of software programming techniques. For example, program sections or program modules can be designed in or by means of Java, Python, C, C++, assembly language, or any known programming languages. One or more of such software sections or modules can be integrated into a computer system and/or computer-readable media. Such software code can include computer readable instructions for performing various methods. The software code may form portions of computer program products or computer program modules. Further, in an example, the software code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

Moreover, while illustrative embodiments have been described herein, the scope includes any and all embodiments having equivalent elements, modifications, omissions, combinations (e.g., of aspects across various embodiments), adaptations or alterations based on the present disclosure. The elements in the claims are to be interpreted broadly based on the language employed in the claims and not limited to examples described in the present specification or during the prosecution of the application, which examples are to be construed as non-exclusive. Further, the steps of the disclosed methods can be modified in any manner, including by reordering steps or inserting or deleting steps. It is intended, therefore, that the specification and examples be considered as example only, with a true scope and spirit being indicated by the following claims and their full scope of equivalents.

The above description is intended to be illustrative, and not restrictive. For example, the above-described examples (or one or more aspects thereof) may be used in combination with each other. Other embodiments can be used, such as by one of ordinary skill in the art upon reviewing the above description. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations.

The invention claimed is:

1. A radiotherapeutic apparatus for volumetric modulated arc therapy (VMAT), the radiotherapeutic apparatus comprising:
a gantry configured to rotate along a trajectory, the trajectory comprising an arc for VMAT, the arc comprising a plurality of control points;
an imaging device configured to capture one or more images depicting anatomical data of a patient; and
a controller configured to perform operations comprising:
receiving an image depicting anatomical data of a target region of patient tissue;
determining an initial prescribed dose of radiotherapeutic radiation to be delivered to the target region;
discretizing the arc for VMAT into a plurality of arc segments, each of the arc segments being between two consecutive control points of the plurality of control points;
performing an iteration process including at least one iteration, each iteration of the iteration process including:
for each of the plurality of arc segments:
performing a fluence optimization process using the anatomical data of the target region and the target region data to generate a distribution profile for a sub-dose to be delivered for the each of the plurality of arc segments based on one of the initial prescribed dose, an updated prescribed dose, or a bias dose that is determined based on the anatomical data;
segmenting the sub-dose distribution profile into segments for delivering the sub-dose to the target region;
identifying, among the segments, one or more non-deliverable segments, each of the one or more non-deliverable segments violating a constraint of the radiotherapeutic apparatus;
replacing the each of the one or more non-deliverable segments with an updated segment, wherein the updated segment does not violate a mechanical or efficiency constraint of the radiotherapeutic apparatus;
determining an arc dose based on the updated segments and the selected segments that do not violate a mechanical or efficiency constraint of the radiotherapeutic apparatus;
delivering radiation to the target region with the determined arc dose along the arc; and
subtracting the determined arc dose from the prescribed dose to generate an updated prescribed dose;
determining whether a condition for terminating the iteration process is met; and
terminating the iteration process based on a result of the determination that the condition for terminating the iteration process is met.

2. The radiotherapeutic apparatus of claim 1, wherein the condition for terminating the iteration process is one of: a number of the iterations of the iteration process performed equals to or exceeds a threshold number; or the updated prescribed dose is equal to or less than a threshold dose.

3. The radiotherapeutic apparatus of claim 1, wherein the controller is configured to terminate treatment based on the result of the determination that the condition for terminating the iteration process is met.

4. The radiotherapeutic apparatus of claim 1, wherein the imaging device is further configured to capture an image depicting updated anatomical data of the patient, at least one of the iterations of the iteration process further comprising:
receiving, from the imaging device, an image depicting updated anatomical data of the target region; and
performing the fluence optimization process using the updated anatomical data of the target region and the target region data to generate a distribution profile for a sub-dose to be delivered in the each of the plurality of arc segments based on a bias dose that is determined based on the updated anatomical data.

5. The radiotherapeutic apparatus of claim 1, wherein the imaging device is further configured to capture an image depicting updated anatomical data of the patient, at least one of the iterations of the iteration process further comprising:
receiving, from the imaging device, an image depicting updated anatomical data of the target region;
determining, based on the updated anatomical data, a bias dose; and determining, based on the determined bias dose, a distribution profile for a sub-dose to be delivered for the each of the plurality of arc segments.

6. The radiotherapeutic apparatus of claim 5, wherein the controller is further configured to perform operations comprising:
adjusting, based on the updated anatomical data, a parameter of the radiotherapeutic apparatus for delivering radiation, wherein performing the iteration process is based, at least in part, on the adjusted parameter.

7. The radiotherapeutic apparatus of claim 6, wherein adjusting, based on the updated anatomical data, the parameter of the radiotherapeutic apparatus for delivering radiation comprises:
determining, based on the updated anatomical data, a log file of the radiotherapeutic apparatus for delivering radiation, wherein performing the iteration process is based, at least in part, on the determined log file.

8. The radiotherapeutic apparatus of claim 1, wherein identifying one or more non-deliverable segments comprises:
identifying a non-deliverable segment that violates a constraint of the radiotherapeutic apparatus when a gantry rotates at a predetermined speed.

9. The radiotherapeutic apparatus of claim 1, wherein identifying one or more non-deliverable segments comprises:
identifying a non-deliverable segment that violates a maximum speed of multi-leaf collimator (MLC) leaves moving between two control points.

10. The radiotherapeutic apparatus of claim 1, wherein the imaging device comprises one of a magnetic resonance image (MRI) device, a cone-beam computed tomography (CBCT) scanner, an ultrasonic device, or an electronic portal imaging device (EPID).

11. A method for radiation delivery to a target region of a patient using a VMAT device, the method comprising:
receiving an image depicting anatomical data of a target region of patient tissue;
determining an initial prescribed dose of radiotherapeutic radiation to be delivered to the target region;
discretizing the arc for VMAT into a plurality of arc segments, each of the arc segments being between two consecutive control points of the plurality of control points;
performing an iteration process including at least one iteration, each iteration of the iteration process including:
for each of the plurality of arc segments:
performing a fluence optimization process using the anatomical data of the target region and the target region data to generate a distribution profile for a sub-dose to be delivered for the each of the plurality of arc segments based on one of the initial prescribed dose, an updated prescribed dose, or a bias dose that is determined based on the anatomical data of the target region;
segmenting the sub-dose distribution profile into segments for delivering the sub-dose to the target region;
identifying, among the segments, one or more non-deliverable segments, each of the one or more non-deliverable segments violating a constraint of the radiotherapeutic apparatus;
replacing the each of the one or more non-deliverable segments with an updated segment, wherein the updated segment does not violate a mechanical or efficiency constraint of the radiotherapeutic apparatus;
determining an arc dose based on the updated segments and the selected segments that do not violate a mechanical or efficiency constraint of the radiotherapeutic apparatus;
delivering radiation to the target region with the determined arc dose along the arc; and
subtracting the determined arc dose from the prescribed dose to generate an updated prescribed dose;
determining whether a condition for terminating the iteration process is met; and
terminating the iteration process based on a result of the determination that the condition for terminating the iteration process is met.

12. The method of claim 11, wherein the condition for terminating the iteration process is one of a number of the iterations of the iteration process performed equals to or exceeds a threshold number; or the updated prescribed dose is equal to or less than a threshold dose.

13. The method of claim 11, further comprising:
terminating treatment based on the result of the determination that the condition for terminating the iteration process is met.

14. The method of claim 11, further comprising receiving an image depicting updated anatomical data of the patient, wherein at least one of the iterations of the iteration process further comprises:
performing the fluence optimization process using the updated anatomical data.

15. The method of claim 11, further comprising receiving an image depicting updated anatomical data of the patient, wherein at least one of the iterations of the iteration process further comprises:
determining, based on the updated anatomical data and one of the initial prescribed dose or the updated prescribed dose, a bias dose; and
determining, based on the determined bias dose, a distribution profile for a sub-dose to be delivered for the each of the plurality of arc segments.

16. The method of claim 15, further comprising:
adjusting, based on the updated anatomical data, a parameter of the radiotherapeutic apparatus for delivering radiation, wherein performing the iteration process is based, at least in part, on the adjusted parameter.

17. The method of claim 16, wherein adjusting, based on the updated anatomical data, the parameter of the radiotherapeutic apparatus for delivering radiation comprises:
determining, based on the updated anatomical data, a log file of the VMAT device for delivering radiation, wherein performing the iteration process is based, at least in part, on the determined log file.

18. The method of claim 11, wherein identifying one or more non-deliverable segments comprises:
identifying a non-deliverable segment that violates a constraint of the radiotherapeutic apparatus when a gantry rotates at a predetermined speed.

19. The method of claim 11, wherein:
the VMAT device comprises a multi-leaf collimator (MLC), and
identifying one or more non-deliverable segments comprises:
identifying a non-deliverable segment that violates a maximum speed of leaves of the MLC moving between two control points.

20. A tangible, non-transitory computer-readable memory device that stores a set of instructions that, when executed by at least one processor, cause the at least one processor to perform operations comprising:

receiving an image depicting anatomical data of a target region of patient tissue;

determining an initial prescribed dose of radiotherapeutic radiation to be delivered to the target region;

discretizing the arc for VMAT into a plurality of arc segments, each of the arc segments being between two consecutive control points of the plurality of control points;

performing an iteration process including at least one iteration, each iteration of the iteration process including:

for each of the plurality of arc segments:

performing a fluence optimization process using the anatomical data of the target region and the target region data to generate a distribution profile for a sub-dose to be delivered for the each of the plurality of arc segments based on one of the initial prescribed dose, an updated prescribed dose, or a bias dose that is determined based on the anatomical data;

segmenting the sub-dose distribution profile into segments for delivery the sub-dose to the target region;

identifying, among the segments, one or more non-deliverable segments, each of the one or more non-deliverable segments violating a constraint of the radiotherapeutic apparatus;

replacing the each of the one or more non-deliverable segments with an updated segment, wherein the updated segment does not violate a mechanical or efficiency constraint of the radiotherapeutic apparatus;

determining an arc dose based on the updated segments and the selected segments that do not violate a mechanical or efficiency constraint of the radiotherapeutic apparatus;

delivering radiation to the target region with the determined arc dose along the arc; and         subtracting the determined arc dose from the prescribed dose to generate an updated prescribed dose;

determining whether a condition for terminating the iteration process is met; and     terminating the iteration process based on a result of the determination that the condition for terminating the iteration process is met.

* * * * *